United States Patent [19]

de Lannoy

[11] 4,216,221
[45] Aug. 5, 1980

[54] 1,3-DISUBSTITUTED (2-THIO)UREAS

[75] Inventor: Jean de Lannoy, Brussels, Belgium

[73] Assignee: U C B, Societe Anonyme, Saint-Gilles-lez-Bruxelles, Belgium

[21] Appl. No.: 876,922

[22] Filed: Feb. 9, 1978

[30] Foreign Application Priority Data

Feb. 10, 1977 [GB] United Kingdom ................ 5494/77

[51] Int. Cl.² ................ C07D 401/12; C07D 403/12; A61K 31/40
[52] U.S. Cl. .......................... 424/274; 260/239.3 B; 260/239.3 R; 260/326.33; 260/326.43; 260/326.5 C; 260/326.5 FL; 424/244; 424/267; 546/15; 546/16; 546/188; 546/205; 546/208; 546/216; 546/221
[58] Field of Search ................ 260/326.25, 239.3 R, 260/326.27, 239.3 B, 326.33; 546/188, 16, 15, 183, 200, 205, 208; 424/274, 267, 244

[56] References Cited

U.S. PATENT DOCUMENTS 2,850,529  9/1958  Pinson ........................... 260/326.25

Primary Examiner—Mary C. Lee
Attorney, Agent, or Firm—Wenderoth, Lind & Ponack

[57] ABSTRACT

A 1,3-disubstituted urea or 2-thiourea having the formula

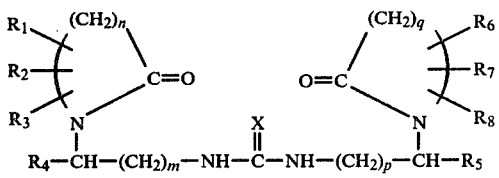

wherein $R_1$, $R_2$, $R_3$, $R_6$, $R_7$ and $R_8$ represent independently a hydrogen atom, an alkyl radical containing 1 to 4 carbon atoms, an alkenyl radical containing 2 to 4 carbon atoms, an alkylene radical forming together with the carbon atom to which it is attached a cycloalkane ring having 5 or 6 carbon atoms, an aryl radical or a substituted aryl radical, $R_4$ and $R_5$ represent independently a hydrogen atom, an alkyl radical containing 1 or 2 carbon atoms or a phenyl radical, n and q are independently a whole number of from 3 to 7, m and p are independently 0, 1 or 2 and X is an oxygen or a sulfur atom, processes for the preparation thereof and pharmaceutical compositions containing the same.

15 Claims, No Drawings

1,3-DISUBSTITUTED (2-THIO)UREAS

The present invention relates to new ureas and 2-thioureas which are substituted on each of the two nitrogen atoms by a straight or branched alkyl group, the latter being, in turn, attached to the nitrogen atom of an unsubstituted or substituted lactam, to processes for the preparation of these compounds, and to their use in the field of therapeutics.

The new 1,3-disubstituted ureas and 2-thioureas have the following general formula:

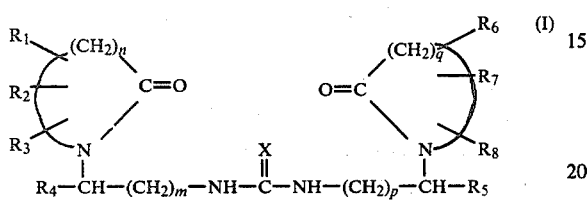

wherein $R_1$, $R_2$, $R_3$, $R_6$, $R_7$ and $R_8$, represent independently, a hydrogen atom, an alkyl radical containing 1 to 4 carbon atoms, an alkenyl radical containing 2 to 4 carbon atoms, an alkylene radical forming together with the carbon atom to which it is attached a cycloalkane ring having 5 or 6 carbon atoms, an unsubstituted aryl radical or an aryl radical which is substituted for example by a halogen atom, $R_4$ and $R_5$ represent independently a hydrogen atom, an alkyl radical containing 1 or 2 carbon atoms or a phenyl radical, n and q, which may be the same or different, are whole numbers of from 3 to 7, m and p, which may be the same or different, are 0, 1 or 2 and X is an oxygen or sulfur atom.

Since n and q are 3, 4, 5, 6 or 7, the lactam groups of the compounds of general formula (I) are, respectively, the 2-oxo-pyrrolidino, 2-oxo-piperidino, hexahydro-2-oxo-1H-azepin-1-yl, hexahydro-2-oxo-1(2H)-azocinyl and octahydro-2-oxo-1H-azonin-1-yl radicals, n and q are preferably 3.

The substituents $R_1$, $R_2$, $R_3$, $R_6$, $R_7$ and $R_8$ may be in any position on the lactam groups. The aryl radicals include in particular the phenyl and naphthyl radicals. The aryl radicals may be substituted, for example, by halogen atoms.

The compounds of general formula (I) possess particularly valuable pharmaceutical properties. In particular, they display a beneficial activity on mnemic processes and a protective activity against aggressions of the hypoxic type. Therefore, their first use is in the field of geropsychiatry, in which disorders of the memory occur due not only to senile cellular alterations but also to a decrease in the supply of oxygen to the brain as the result of isolated or repeated vascular accidents (see, for example, V. C. HACHINSKI, Lancet, II,(1974),207). Furthermore, the compounds of general formula (I) are useful in numerous other clinical fields, such as the prevention and treatment of cerebrovascular or cardiovascular injuries, post-traumatic or toxic comas, memory disorders, difficulties in mental concentration and the like. Finally, these new compounds display an interesting activity in the field of blood platelet aggregation. They are, in fact, blood platelet anti-aggregants and they can, therefore, also be used in the treatment of myocardial infarcts resulting from blood platelet hyperaggregability or hyperadhesivity, in extracorporal circulations, in the case of vascular prostheses, or in the treatment of thrombo-embolic diseases or hyperaggregability in coronary patients.

Compounds are already known which have properties of the same type, particularly piracetam (2-oxo-1-pyrrolidineacetamide; see British Pat. No. 1,039,113). However, this compound has the disadvantage of being effective only in high doses. One of the objects of the present invention is, therefore, to provide compounds having the same advantageous properties as piracetam but which are effective in much smaller doses.

The compounds of general formula (I) can be prepared by a general process, which comprises reacting an N-(aminoalkyl)lactam of the formula

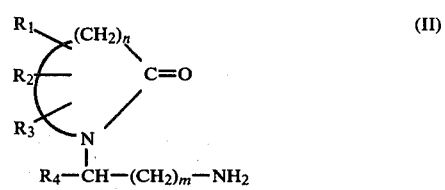

wherein $R_1$, $R_2$, $R_3$, $R_4$, n and m have the meanings given above, and an N-(aminoalkyl)lactam of the formula

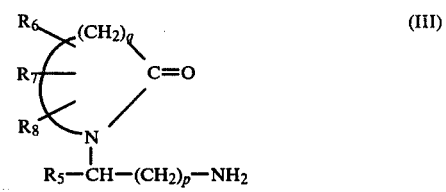

wherein $R_5$, $R_6$, $R_7$, $R_8$, q and p have the meanings given above, with a (thio)-carbonyl compound of the formula

wherein X has the meaning given above and Y and Z are each a halogen atom or an imidazolyl group or Y is a halogen atom and Z an alkoxy radical having 1 to 4 carbon atoms, in an inert medium in the presence of a basic condensation agent, to obtain the desired compounds of general formula (I).

When the symbols Y and Z are each a halogen atom, the compound of formula (IV) is preferably phosgene (X=O, Y=Z=Cl) or thiophosgene (X=S, Y=Z=Cl).

When the symbols Y and Z are each an imidazolyl group, the compound of formula (IV) is preferably 1,1'-carbonyldiimidazole (X=O, Z=Z=imidazolyl) or 1,1'-thiocarbonyldiimidazole (X=S, Y=Z=imidazolyl).

Whe the symbol Y is a halogen atom and Z an alkoxy radical having 1 to 4 carbon atoms, the compound of formula (IV) is an alkyl haloformate (X=O, Y=halogen, Z=alkoxy), preferably ethyl chloroformate.

Besides the general process for the preparation of the compounds of formula (I) mentioned hereinabove, other particular processes may be used to prepare symmetric compounds of formula (I); i.e. wherein $R_1=R_6$, $R_2=R_7$, $R_3=R_8$, $R_4=R_5$, n=q and m=p.

According to a first embodiment, the general process mentioned above is followed but using 2 moles of the N-(aminoalkyl)lactam of formula (II) with 1 mole of the (thio)carbonyl compound of formula (IV), all other operating conditions remaining unchanged.

On the other hand, when it is desired to prepare symmetric 1,3-disubstituted ureas of the general formula (I), wherein X=oxygen, the process comprises reacting a lactam-N-alkanoic acid chloride of the formula

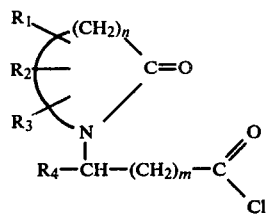
(V)

wherein $R_1$, $R_2$, $R_3$, $R_4$, n and m have the meanings given above, with an organosilyl ozide, such as trimethylsilyl azide, and then hydrolyzing and selectively decarboxylating the resulting lactam-N-alkyl isocyanate of the formula

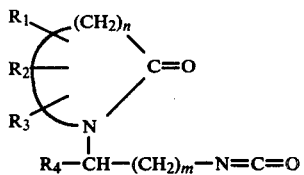
(VI)

wherein $R_1$, $R_2$, $R_3$, $R_4$, n and m have the meanings given above, to give the following compounds of formula (I)

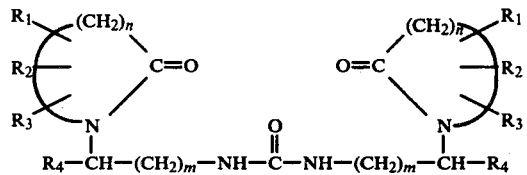

Furthermore, when it is desired to prepare a symmetric 1,3-disubstituted urea or 2-thiourea of general formula (I), the process comprises reacting 2 moles of a lactam of the formula

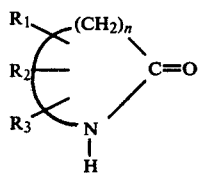
(VII)

wherein $R_1$, $R_2$, $R_3$ and n have the meanings given above, with one mole of a 1,3-bis(hydroxyalkyl)-(2-thio)urea of the formula

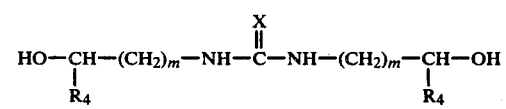
(VIII)

wherein X, $R_4$ and m have the meanings given above, to give the following symmetric compounds of formula (I)

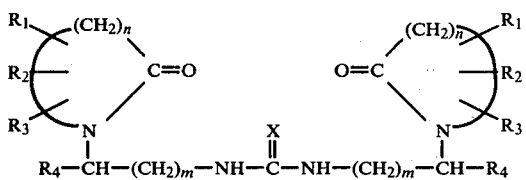

Finally, when it is desired to prepare a symmetric 1,3-disubstituted urea of general formula (I), wherein X=oxygen, $R_4$=$R_5$=hydrogen, m=p=zero the process comprises reacting together 1 mole of urea, 2 moles of formaldehyde and 2 moles of a lactam of the formula (VII) according to the following equation:

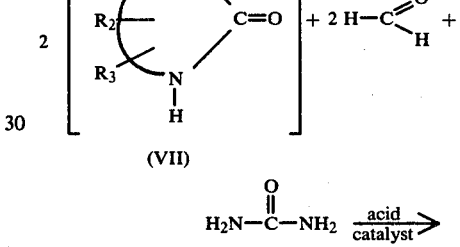

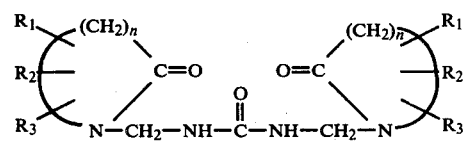

wherein $R_1$, $R_2$, $R_3$ and n have the meanings given above.

Certain $R_1$, $R_2$, $R_3$, $R_4$-substituted or $R_5$, $R_6$, $R_7$, $R_8$-substituted N-(aminoalkyl)lactams of the formulae (II) and (III), respectively, which are starting compounds in the synthesis of the compounds of general formula (I), have already been described in literature. Thus, for example, 1-(2-aminoethyl)-2-pyrrolidinone is described by W. REPPE et al., in Liebigs Ann., 596, (1955), 203 and 1-(3-aminopropyl)-2-pyrrolidinone is described in Chemical Abstracts, 53, (1959), 4816. Those compounds which have not yet been described in literature may all be prepared by any of the following known methods:

method A: ammonolysis of a halogenated compound;
method B: Hofmann reaction on an amide;
method C: reduction of a nitrile.

In each of the methods A, B and C, the halogenated compounds, the amides and the nitriles are obtained from appropriate $R_1$, $R_2$, $R_3$-substituted or $R_6$, $R_7$, $R_8$-substituted lactams, respectively.

EXPERIMENTAL PART

I. Preparation of N-(aminoalkyl)lactams of general formula (II)

I.1. Ammonolysis of a halogenated compound (method A)

I.1.1. Preparation of N-hydroxymethyl-lactams.

This process has already been described in literature (see, for example, Chem. Abstr. 54, (1960), 1286e) and has been modified as follows:

A 35% aqueous solution of formaldehyde is added to a solution of lactam in ethanol, which has been made basic by means of sodium hydroxide, at a rate such that the temperature does not exceed 40° C. The reaction mixture is then brought to the boil under reflux and subsequently concentrated under reduced pressure. The residue obtained is taken up in ethanol and re-concentrated in order to remove the last traces of water and formaldehyde.

Thus, for example, 1-hydroxymethyl-2-pyrrolidinone was prepared in the following manner. A solution of 1355 g (15.94 moles) of 2-pyrrolidinone and 30 g (0.75 mole) of sodium hydroxide in 2.8 liters absolute ethanol was placed in a 20 liter 3-necked flask. 5250 (56.35 moles) of a 35% aqueous solution of formaldehyde were added slowly thereto. The temperature of the reaction mixture increased progressively during the course of the addition and stabilized at about 40° C. When the addition had been completed, the solution was brought to the boil under reflux for 5 and a half hours. The ethanol and excess formaldehyde were eliminated under reduced pressure. The residue was taken up in 1.2 liter of hot absolute ethanol and the solution was clarified by filtration through a Hyflo-cel filter. The solvent was evaporated under reduced pressure and the residue was recrystallized from the minimum amount of isopropyl alcohol. 1575 g (86% of theory) of 1-hydroxymethyl-2-pyrrolidinone were obtained; M.P. 83°–84° C.

I.R. spectrum (KBr) in cm$^{-1}$: 3280, 2990, 2950, 2900, 1665, 1395, 1045.

The following compounds were prepared in the same manner:

(a) hexahydro-1-hydroxymethyl-2H-azepin-2-one (Yield: 47% of theory); I.R. spectrum (KBr) in cm$^{-1}$: 3260, 2940, 2840, 1630, 1030. This compound is already described in literature (see R. E. BENSON and T. L. CAIRNS, J. Am. Chem. Soc. 70, (1948), 2115-8).

(b) 1-hydroxymethyl-2-piperidinone (Yield: 90% of theory); I.R. spectrum (film) in cm$^{-1}$: 3320, 2940, 2870, 1630, 1045.

(c) 1-hydroxymethyl-5-methyl-2-pyrrolidinone (Yield: 78% of theory); I.R. spectrum (film) in cm$^{-1}$: 3360, 2970, 2900, 1680, 1630.

(d) octahydro-1-hydroxymethyl-2H-azonin-2-one (Yield: 95% of theory); I.R. spectrum (film) in cm$^{-1}$: 3340, 2930, 2870, 1630, 1040.

(e) hexahydro-1-hydroxymethyl-2(1H)-azocinone (Yield: 99% of theory); I.R. spectrum (film) in cm$^{-1}$: 3340, 2930, 2880, 1630, 1040.

(f) 4-p-chlorophenyl-1-hydroxymethyl-3-methyl-2-pyrrolidinone (Yield: 59% of theory); I.R. spectrum (film) in cm$^{-1}$: 3360, 3020, 2970, 2930, 2880, 1680, 1040, 910, 890.

(g) 1-hydroxymethyl-3,5-dimethyl-2-pyrrolidinone (Yield: 45% of theory); I.R. spectrum (film) in cm$^{-1}$: 3360, 2970, 2930, 2870, 1670, 1040.

(h) 1-hydroxymethyl-4,5-dimethyl-2-pyrrolidinone (Yield: 78% of theory); I.R. spectrum (film) in cm$^{-1}$: 3350, 2970, 2950, 2880, 1750, 1420, 1045.

(i) 3-allyl-1-hydroxymethyl-3-phenyl-2-pyrrolidinone (Yield: 85% of theory); I.R. spectrum (film) in cm$^{-1}$: 3400, 3080, 2980, 2950, 2900, 1680, 1435, 1275, 1040, 700.

(j) 1-hydroxymethyl-4-phenyl-2-pyrrolidinone (Yield: 71% of theory); I.R. spectrum (KBr) in cm$^{-1}$: 3270, 2955, 2880, 1685, 1440, 1025, 710, 660.

(k) 3-ethyl-1-hydroxymethyl-3-phenyl-2-pyrrolidinone (Yield: 92% of theory); I.R. spectrum (film) in cm$^{-1}$: 3380, 3060, 2970, 2880, 1675, 1460, 765, 700.

(l) 5-p-chlorophenyl-1-hydroxymethyl-2-piperidinone (Yield: 83% of theory); I.R. spectrum (KBr) in cm$^{-1}$: 3300, 2990, 2940, 2880, 1630, 1440, 1050, 840, 830.

(m) 1-hydroxymethyl-3,5,5-trimethyl-2-pyrrolidinone (Yield: 55% of theory); I.R. spectrum (film) in cm$^{-1}$: 3370, 2970, 2930, 2870, 1670, 1045.

(n) 2-hydroxymethyl-3-methyl-2-azaspiro[4.5]decan-1-one (Yield: 91% of theory); I.R. spectrum (film) in cm$^{-1}$: 3380, 2970, 2930, 2860, 1675, 1450, 1010.

(o) 3-n-butyl-1-hydroxymethyl-2-pyrrolidinone (Yield: 99% of theory); I.R. spectrum (film) in cm$^{-1}$: 3370, 2960, 2880, 1680, 1465.

I.1.2. Preparation of N-chloromethyl-lactams (a) 1-Chloromethyl-2-piperidinone.

618 ml (8.6 mole of thionyl chloride are added dropwise, with vigorous stirring, to a solution of 903 g (7 mole) of 1-hydroxymethyl-2-piperidinone in 6000 ml of anhydrous benzene, taking care that the temperature does not exceed 10° C. After the addition, the reaction is continued for 2 hours at ambient temperature. The mixture is filtered through Hyflo-cel filter and the filtrate is evaporated under reduced pressure and then dissolved three times in anhydrous benzene, the benzene solution being evaporated each time under reduced pressure in order to remove the last traces of thionyl chloride and hydrogen chloride (which is formed in the course of the reaction). The oily residue is first degasified under a pressure of 15 mm Hg and then purified by distillation (143°–145° C./15 mm Hg), 640 g (4.34 mole) of 1-chloromethyl-2-piperidinone being obtained. (Yield: 62% of theory); I.R. spectrum (film) in cm$^{-1}$: 2950, 2870, 1660.

The following N-chloromethyl-lactams are prepared by the same process:

(b) 1-chloromethyl-2-pyrrolidinone (Yield: 87% of theory); I.R. spectrum (film) in cm$^{-1}$: 3038, 2970, 2885, 1700, 1260.

(c) 1-chloromethyl-hexahydro-2H-azepin-2-one (Yield: 99% of theory). B.P. 118°–120° C./3.5-4 mm Hg. This compound has already been described in literature (see F. L. SIDEL'KOVSKAYA et al., Chem. Abstr. 54, (1960), 1286).

(d) 1-chloromethyl-hexahydro-2(1H)-azocinone (Yield: 32% of theory); I.R. spectrum (film) in cm$^{-1}$: 2930, 2860, 1660.

(e) 1-chloromethyl-octahydro-2H-azonin-2-one (Yield: 81% of theory); I.R. spectrum (film) in cm$^{-1}$: 3020, 2930, 2882, 1660, 1255.

(f) 1-chloromethyl-5-methyl-2-pyrrolidinone (Yield: 54% of theory); I.R. spectrum (film) in cm$^{-1}$: 2970, 2880, 1740.

(g) 1-chloromethyl-4-p-chlorophenyl-3-methyl-2-pyrrolidinone (Yield: 68% of theory); I.R. spectrum (film) in cm$^{-1}$: 3030, 2970, 2930, 2870, 1710, 900, 830.

(h) 1-chloromethyl-3,5-dimethyl-2-pyrrolidinone (Yield: 77% of theory); I.R. spectrum (film) in cm$^{-1}$: 2970, 2930, 2880, 1700.

(i) 1-chloromethyl-4,5-dimethyl-2-pyrrolidinone (Yield: 28% of theory); I.R. spectrum (film) in cm$^{-1}$: 2970, 2930, 2880, 1715.

(j) 3-allyl-1-chloromethyl-3-phenyl-2-pyrrolidinone (Yield: 91% of theory); I.R. spectrum (film) in cm$^{-1}$: 3060, 3040, 2980, 2890, 1710, 1270, 700.

(k) 1-chloromethyl-4-phenyl-2-pyrrolidinone (Yield: 96% of theory); I.R. spectrum (film) in cm$^{-1}$: 3060, 3030, 2980, 2950, 2880, 1715, 1255, 765, 700.

(l) 1-chloromethyl-3-ethyl-3-phenyl-2-pyrrolidinone (Yield: 78% of theory); I.R. spectrum (film) in cm$^{-1}$: 3060, 3040, 2970, 2880, 1700, 1265, 765, 700.

(m) 1-chloromethyl-5-p-chlorophenyl-2-piperidinone (Yield: 46% of theory); I.R. spectrum (film) in cm$^{-1}$: 3040, 2940, 2900, 1670, 1480, 830, 800.

(n) 1-chloromethyl-3,5,5-trimethyl-2-pyrrolidinone (Yield: 34% of theory); I.R. spectrum (film) in cm$^{-1}$: 2970, 2940, 2880, 1715.

(o) 2-chloromethyl-3-methyl-2-azaspiro[4.5]decan-1-one (Yield: 93% of theory); I.R. spectrum (film) in cm$^{-1}$: 2970, 2930, 2860, 1710, 1450.

(p) 3-n-butyl-1-chloromethyl-2-pyrrolidinone (Yield: 62% of theory); I.R. spectrum (film) in cm$^{-1}$: 2960, 2880, 1720.

I.1.3. Preparation of N-(aminomethyl)lactams

The ammonolysis of an N-chloromethyl-lactam is carried out by slowly introducing, with vigorous stirring, a solution of the compound in toluene into a large excess of liquid ammonia at $-30°$ C. The reaction is accompanied by the formation of ammonium chloride, which precipitates. The ammonia is then evaporated and the solution is filtered and distilled under reduced pressure in order to eliminate the toluene. The resulting N-(aminomethyl)lactam can be used as it is for the synthesis of compounds of general formula (I) according to the present invention.

(a) 1-aminomethyl-hexahydro-2(1H)-azocinone.

A solution of 526.8 g (3 moles) of 1-chloromethyl-hexahydro-2(1H)-azocinone in 1.5 liter of anhydrous toluene is added dropwise, with vigorous stirring, to 2 liters of liquid ammonia. After the addition, the ammonia is evaporated, the ammonium chloride is filtered off and the filtrate is evaporated under reduced pressure. The oily residue obtained is taken up twice in 1 liter anhydrous toluene and the solution is evaporated under reduced pressure each time. 463.3 g (2.97 moles) of a limpid yellow oil are thus obtained. (Yield: 99% of theory). I.R. spectrum (film) in cm$^{-1}$: 3400, 3320, 2930, 2860, 1635, 1470.

The following compounds are prepared in the same manner:

(b) 1-aminomethyl-2-pyrrolidinone. Yield: 98% of theory; I.R. spectrum (film) in cm$^{-1}$: 3380, 3310, 2940, 2880, 1675, 1470, 1260.

(c) 1-aminomethyl-2-piperidinone. Yield: 98% of theory; I.R. spectrum (film) in cm$^{-1}$: 3380, 2940, 2870, 1635.

(d) 1-aminomethyl-hexahydro-2H-azepin-2-one. Yield: 89% of theory; I.R. spectrum (film) in cm$^{-1}$: 3390, 3320, 2940, 2860, 1640, 1490, 1440.

(e) 1-aminomethyl-octahydro-2H-azonin-2-one. Yield: 46% of theory; I.R. spectrum (film) in cm$^{-1}$: 3395, 3320, 2930, 2880, 1630, 1440.

(f) 1-aminomethyl-4-p-chlorophenyl-3-methyl-2-pyrrolidinone. Yield: 95% of theory; I.R. spectrum (film) in cm$^{-1}$: 3380, 3030, 2980, 2930, 2870, 1680, 830, 870.

(g) 1-aminomethyl-5-methyl-2-pyrrolidinone. Yield: 52% of theory; I.R. spectrum (film) in cm$^{-1}$: 3380, 3320, 2970, 2880, 1680.

(h) 1-aminomethyl-4-phenyl-2-pyrrolidinone. Yield: 98% of theory; I.R. spectrum (film) in cm$^{-1}$: 3360, 3310, 3030, 2970, 2940, 2870, 1660, 1260, 700, 650.

(i) 1-aminomethyl-3-ethyl-3-phenyl-2-pyrrolidinone. Yield: 70% of theory; I.R. spectrum (film) in cm$^{-1}$: 3380, 3320, 2960, 2940, 2880, 1680, 1490, 770, 700.

(j) 1-aminomethyl-4,5-dimethyl-2-pyrrolidinone. Yield: 65% of theory; I.R. spectrum (film) in cm$^{-1}$: 3380, 3320, 2970, 2930, 2880, 1680, 1260.

(k) 3-allyl-1-aminomethyl-3-phenyl-2-pyrrolidinone. Yield: 90% of theory; I.R. spectrum (film) in cm$^{-1}$: 3390, 3220, 3060, 2980, 2940, 2880, 1680, 1250, 700.

(l) 1-aminomethyl-5-p-chlorophenyl-2-piperidinone. Yield: 87% of theory; I.R. spectrum (film) in cm$^{-1}$: 3380, 3300, 2940, 2900, 2870, 1670, 1490, 830, 810.

(m) 1-aminomethyl-3-n-butyl-2-pyrrolidinone. Yield: 89% of theory; I.R. spectrum (film) in cm$^{-1}$: 3380, 3320, 2960, 2880, 1680, 1495, 1460.

(n) 1-aminomethyl-3,5,5-trimethyl-2-pyrrolidinone. Yield: 37% of theory; I.R. spectrum (film) in cm$^{-1}$: 3390, 3320, 2970, 2930, 2870, 1680.

(o) 2-aminomethyl-3-methyl-2-azaspiro[4.5]decan-1-one. Yield: 95% of theory; I.R. spectrum (film) in cm$^{-1}$: 3390, 3320, 2970, 2930, 2860.

I.2. Hofmann reaction on an amide (method B)

(a) Preparation of 1-aminomethyl-5-phenyl-2-pyrrolidinone.

19.98 g (0.125 mole) of bromine are added, with vigorous stirring, to a mixture composed of a solution of 21.8 g (0.1 mole) of 2-oxo-5-phenyl-1-pyrrolidinacetamide and a solution of 15.28 g (0.382 mole) of sodium hydroxide in 250 ml of water, while ensuring that the temperature does not exceed 10° C. After the addition, the reaction mixture is stirred for 2 hours at ambient temperature and for 2 hours under reflux. It is then lyophilized and the residue is mixed with 500 ml of absolute ethanol and filtered in order to remove mineral salts. The ethanolic solution is evaporated under reduced pressure and the remaining oil is dissolved in methylene chloride, filtered through a Hyflo-cel filter and the filtrate evaporated to dryness under reduced pressure. 13.7 g (0.072 mole) of 1-aminomethyl-5-phenyl-2-pyrrolidinone are obtained. Yield: 72% of theory. I.R. spectrum (film) in cm$^{-1}$: 3350, 3060, 2950, 1670, 760, 735, 700.

According to the same process, the following compounds are prepared:

(b) 1-aminomethyl-2-pyrrolidinone (this is the same compound as in paragraph I.1.3.b above). Yield: 68% of theory.

(c) 1-(1-aminopropyl)-2-pyrrolidinone.

This compound can be used as it is, without being isolated.

(d) 1-(1-aminoethyl)-2-pyrrolidinone.

This compound can be used as it is, without being isolated.

(e) 1-(alpha-aminobenzyl)-2-pyrrolidinone.

This compound can be used as it is, without being isolated.

I.3. Reduction of a nitrile (method C)

(a) Preparation of 1-(2-amino-1-methylethyl)-2-pyrrolidinone.

0.1 g of sodium hydroxide and 1 g of Raney nickel are added to a solution of 13 g (0.094 mole) of alpha-methyl-2-oxo-1-pyrrolidineacetonitrile in 250 ml of methanol and hydrogenated at ambient temperature and pressure until there is no further absorption of hydrogen. The catalyst is then filtered off through a Hyflo-cel filter and the filtrate is evaporated under reduced pressure. 9.2 g (0.065 mole) of 1-(2-amino-1-methylethyl)-2-pyrrolidinone are obtained, this product being used as it is for continuing the synthesis (Yield: 69% of theory). I.R. spectrum (film) in cm$^{-1}$: 3380, 2970, 2930, 2870, 1670, 1290.

The following compounds of general formula (II) were prepared in the same manner:

(b) 1-(2-aminoethyl)-2-pyrrolidinone. Yield: 57% of theory; I.R. spectrum (CHCl$_3$) in cm$^{-1}$: 3380, 2990, 2940, 2870, 1660, 1290.

(c) 1-[1-(aminomethyl)propyl]-2-pyrrolidinone. Yield: 75% of theory; I.R. spectrum (film) in cm$^{-1}$: 3370, 2960, 2930, 2870, 1670.

II. Preparation of compounds of general formula (I)

II.1. Action of phosgene or thiophosgene on N-(aminoalkyl)lactams of formula (II)

II.1.1. Action of phosgene (a) 1,3-bis[(2-oxo-pyrrolidino)methyl]-urea. (Compound No. 1)

Method 1

A solution of 232.2 g (2.347 moles) of phosgene in 1 liter methylene chloride, cooled to −10° C. is added slowly and with vigorous stirring to a solution of 802 g (7.03 moles) of 1-aminomethyl-2-pyrrolidinone and 521.2 g (5.16 moles) of triethylamine in 5 liters of anhydrous methylene chloride kept at −10° C., care being taken that the temperature does not exceed 5° C. After the addition, the reaction mixture is allowed to return to ambient temperature and is then again cooled to −10° C. Gaseous ammonia is introduced in order to liberate triethylamine from its hydrochloride. The ammonium chloride formed is filtered (123 g thereof are recovered, i.e. 98% of theory) and the filtrate is evaporated to dryness under reduced pressure. The residue is recrystallized from 2 liters of isopropyl alcohol. 384 g (yield 64.4% of theory) pure 1,3-bis[(2-oxo-pyrrolidino)methyl]-urea (compound No. 1) are thus obtained; M.P. 184.5° C.

Analysis for C$_{11}$H$_{18}$N$_4$O$_3$ (M.W. 254): calculated: C 51.9%, H 7.1%, N 22.0%. found: C 51.9%, H 7.0%, N 21.9%.

I.R. spectrum (KBr) in cm$^{-1}$: 3350, 2900, 1680, 1645, 1565.

Method 2

50 ml of a saturated aqueous solution of sodium carbonate are added to 20.6 g (0.18 mole) of 1-aminomethyl-2-pyrrolidinone in 100 ml of methylene chloride. A solution of 5.95 g (0.06 mole) of phosgene in 50 ml of methylene chloride is added, with vigorous stirring, to this suspension, care being taken that the temperature of the reaction mixture remains below 10° C. After the addition, stirring is continued at ambient temperature for 4 hours. The aqueous phase is decanted, lyophilized and then extracted several times with methylene chloride. The organic extracts are combined and evaporated under reduced pressure. The residue is recrystallized from the minimum of isopropyl alcohol to give 7.2 g (0.0283 mole) of pure compound No. 1 having the same characteristics as before. Yield: 47.2% of theory.

Method 3

A solution of 3.6 g (0.036 mole) of phosgene in 100 ml of methylene chloride is added dropwise to a solution of 27 g (0.145 mole) of 1-aminomethyl-2-pyrrolidinone and 57 g (0.72 mole) of anhydrous pyridine in 300 ml of methylene chloride, care being taken that the temperature of the reaction mixture does not exceed 0° C. The reaction mixture is refluxed for 2 hours and then evaporated to dryness under reduced pressure. The residue is purified by chromatography on silica, using, as eluent, a 10:1 mixture of chloroform and methanol. The product obtained is recrystallized from the minimimum amount of isopropyl alcohol. 3.5 g (0.0138 mole) of compound No. 1 are thus obtained having the same characteristics as before. Yield: 38% of theory.

(b) 1-[(2-oxo-pyrrolidino)methyl]-3-[3-(2-oxo-pyrrolidino)propyl]-urea. (Compound No. 2).

12.42 g (0.123 mole) of triethylamine and 6.39 g (0.056 mole) of 1-aminomethyl-2-pyrrolidinone dissolved in 20 ml of methylene chloride, are introduced successively into a solution of 5.55 g (0.056 mole) of phosgene cooled to −70° C. The mixture is stirred for 30 minutes, care being taken that the temperature does not exceed −60° C. A solution of 7.97 g (0.056 mole) of 1-(3-aminopropyl)-2-pyrrolidinone in 20 ml of methylene chloride is then added thereto. After the addition, the suspension is stirred for 1 hour at ambient temperature and then cooled to −60° C., at which temperature triethylamine hydrochloride crystallizes. The precipitate is filtered off and the filtrate evaporated to dryness under reduced pressure. The residue is chromatographed on a silica column (eluent: acetone-methanol, 96:4). 3.1 g of an oily product are obtained, which is the desired 1[(2-oxopyrrolidino)methyl]-3-[3-(2-oxo-pyrrolidino)propyl]-urea. Yield: 19.6% of theory.

Analysis for C$_{13}$H$_{22}$N$_4$O$_3$ (M.W. 282): calculated: C 55.3%, H 7.9%, N 19.8%. found: C 55.3%, H 7.9%, N 19.1%.

I.R. spectrum (film) in cm$^{-1}$: 3380, 2970, 2930, 1680, 1550, 1500.

The following compounds of general formula (I) are prepared in the same manner:

(c) 1,3-bis[(2-oxo-piperidino)methyl]-urea. (Compound No. 3).

Yield: 34% of theory; M.P. 161°–162° C.

Analysis for C$_{13}$H$_{22}$N$_4$O$_3$: calculated: C 55.3%; H 7.8%, N 19.8%. found: C 55.0%, H 7.9%, N 19.9%.

(d) 1,3-bis[(hexahydro-2-oxo-1H-azepin-1-yl)methyl]-urea. (Compound No. 4).

Yield: 34% of theory; M.P. 169°–170° C.

Analysis for C$_{15}$H$_{26}$N$_4$O$_3$: calculated: C 58.1%, H 8.5%, N 18.1%. found: C 58.9%, H 8.5%, N 18.1%.

(e) 1,3bis[(hexahydro-2-oxo-1(2H)-azocinyl)methyl]-urea. (Compound No. 5).

Yield: 41% of theory; M.P. 224°–225° C.

Analysis for C$_{17}$H$_{30}$N$_4$O$_3$: calculated: C 60.3%, N 8.9%, N 16.5%. found: C 60.4%, N 8.8%, N 16.5%.

(f) 1,3-bis[(octahydro-2-oxo-1H-azonin-1-yl)methyl]-urea. (Compound No. 6).

Yield: 48% of theory; M.P. 207°–208° C.

Analysis for C₁₉H₃₄N₄O₃: calculated: C 62.3%, H 9.4%, N 15.3%. found: C 62.0%, H 9.4%, N 15.3%.

(g) 1,3-bis[(4-p-chlorophenyl-3-methyl-2-oxo-pyrrolidino)methyl]-urea. (Compound No. 7).

Yield: 36% of theory; M.P. 202°–203° C.

Analysis for C₂₅H₂₈Cl₂N₄O₃: calculated: C 59.6%, H 5.6%, H 11.1%, Cl 14.1%. found: C 59.2%, H 5.5%, H 11.0%, Cl 14.7%.

(h) 1,3-bis[(5-methyl-2-oxo-pyrrolidino) methyl]-urea. (Compound No. 8).

Yield: 7% of theory; M.P. 120°–121° C.

Analysis for C₁₃H₂₂N₄O₃: calculated: C 55.3%, H 7.9%, N 19.9%. found: C 55.3%, H 7.8%, N 19.7%.

(i) 1,3-bis[(2-oxo-5-phenyl-pyrrolidino)methyl]-urea. (Compound No. 9).

Yield: 33% of theory; M.P. 190°–192° C.

Analysis for C₂₃H₂₆N₄O₃: calculated: C 67.9%, H 6.4%, N 13.8%. found: C 67.3%, H 6.4%, N 13.7%.

(j) 1,3-bis[1-(2-oxo-pyrrolidino)propyl]-urea. (Compound No. 10).

Yield: 52% of theory; M.P. 130°–131° C.

Analysis for C₁₅H₂₆N₄O₃: calculated: C 58.0%, H 8.4%, N 18.1%. found: C 57.9%, H 8.5%, N 17.9%.

(k) 1,3-bis[1-(2-oxo-pyrrolidino)ethyl]-urea. (Compound No. 11).

Yield: 15% of theory; M.P. 158°–159° C.

Analysis for C₁₃H₂₂N₄O₃: calculated: C 55.3%, H 7.9%, N 19.8%. found: C 55.2%, H 7.9%, N 19.7%.

(l) 1,3-bis[(2-oxo-4-phenyl-pyrrolidino)methyl]-urea. (Compound No.12).

Yield: 60% of theory; M.P. 188°–189° C.

Analysis for C₂₃H₂₆N₄O₃: calculated: C 68.0%, H 6.4%, N 13.8%. found: C 68.0%, H 6.5%, N 13.8%.

(m) 1,3-bis[(3-ethyl-2-oxo-3-phenyl-pyrrolidino)methyl]-urea. (Compound No.13).

Yield: 64% of theory.

Analysis for C₂₇H₃₄N₄O₃: calculated: C 70.1%, H 7.4%, N 12.1%. found: C 69.3%, H 7.0%, N 11.7%.

I.R. spectrum (film) in cm⁻¹: 3360, 3060, 2980, 2950, 2880, 1680, 1560, 760,700.

(n) 1,3-bis[(4,5-dimethyl-2-oxo-pyrrolidino)methyl]-urea. (Compound No.14).

Yield: 22% of theory; I.R. spectrum (film) in cm⁻¹: 3350, 2970, 2880, 1710, 1670, 1550.

(o) 1,3-bis[(3-allyl-2-oxo-3-phenyl-pyrrolidino)methyl]-urea. (Compound No.15).

Yield: 36% of theory; M.P. 134°–135° C.

Analysis for C₂₉H₃₄N₄O₃: calculated: C 71.6%, H 7.0%, N 11.5%. found: C 71.5%, H 7.0%, N 11.5%.

(p) 1,3-bis[(5-p-chlorophenyl-2-oxo-piperidino)methyl]-urea. (Compound No.16).

Yield: 56% of theory; M.P. 202°–203° C.

Analysis for C₂₅H₂₈Cl₂N₄O₃: calculated: C 59.6%, H 5.6%, N 11.1%, Cl 14.1%. found: C 59.6%, H 5.7%, N 11.1%, Cl 14.0%.

(q) 1,3-bis[(3-methyl-1-oxo-2-azaspiro[4.5]dec-2-yl)methyl]-urea. (Compound No.17).

Yield: 46% of theory; M.P. 152°–153° C.

Analysis for C₂₃H₃₈N₄O₃: calculated: C 66.0%, H 9.2%, N 13.4%. found: C 66.0%, H 9.2%, N 13.3%.

(r) 1,3-bis[(3,5,5-trimethyl-2-oxo-pyrrolidino)methyl]-urea. (Compound No.18).

Yield: 45% of theory; M.P. 156°–159° C.

Analysis for C₁₇H₃₀N₄O₃: calculated: C 60.3%, H 8.9%, N 16.5%. found: C 60.3%, H 8.9%, N 16.5%.

(s) 1,3-bis[alpha-(2-oxo-pyrrolidino)-benzyl]-urea. (Compound No.19).

Yield: 33% of theory; M.P. 195°–197° C.

Analysis for C₂₃H₂₆N₄O₃: calculated: C 68.1%, H 6.4%, N 13.8%. found: C 67.5%, H 6.3%, N 13.2%.

(t) 1,3-bis[2-(2-oxo-pyrrolidino)ethyl]-urea. (Compound No.20).

Yield: 51% of theory; M.P. 50°–52° C.

Analysis for C₁₃H₂₂N₄O₃: calculated: C 55.3%, H 7.8%, N 19.8%. found: C 55.1%, H 8.0%, N 19.2%.

(u) 1,3-bis[2-(2-oxo-pyrrolidino)propyl]-urea. (Compound No.21).

Yield: 43% of theory. I.R. spectrum (film) in cm⁻¹: 3360, 2980, 2930, 2870, 1660,1550.

(v) 1,3-bis[(2-(2-oxo-pyrrolidino)butyl]-urea. (Compound No.22).

Yield: 55% of theory.

This compound is in the form of a non-distillable oil.

Mass spectrum: m/e 338, 253, 183, 170, 140, 139, 126, 112, 98.

NMR spectrum (CDCl₃+TMS):

| Chemical shift | Multiplicity | Integration | Attribution |
|---|---|---|---|
| 0.87 ppm | triplet | 6H | (CH₃ in the 4-position of the two butyl radicals) |
| 1.50 ppm | multiplet | 4H | (CH₂ in the 3-position of the two butyl radicals) |
| 1.7–2.7 ppm | multiplet | 8H | (CH₂ in the 3 and 4-positions of the 2 pyrrolidino rings) |
| 2.98–3.77 ppm | multiplet | 8H | (CH₂ in the 1-position of the two butyl radicals and in the 5-position of the two pyrrolidino rings) |
| 4.0 ppm | multiplet | 2H | (CH in the 2-position of the two butyl radicals) |
| 5.5 ppm | broad | 2H | (two NH) |

I.R. spectrum (film) in cm⁻¹: 3370, 2960, 2930, 2870, 1660, 1560.

(w) 1,3-bis[3-(2-oxo-pyrrolidino)propyl]-urea. (Compound No.23).

Yield: 41% of theory; M.P. 87°–88° C.

Analysis for C₁₅H₂₆N₄O₃: calculated: C 58.0%, H 8.4%, N 18.1%. found: C 58.0%, H 8.5%, N 18.2%.

II.1.2. Action of thiophosgene (a) 1,3-bis[(5-p-chlorophenyl-2-oxo-piperidino)methyl]-2-thiourea. (Compound No.24).

A solution of 1.334 g (0.0116 mole) of thiophosgene in 10 ml of methylene chloride is added slowly and with vigorous stirring to a solution of 6.9 g (0.029 mole) of 1-aminomethyl-5-p-chlorophenyl-2-piperidinone and 2.34 g (0.023 mole) of triethylamine in 50 ml of methylene chloride kept at a low temperature (−20° C.). After the addition, the reaction mixture is allowed to return to ambient temperature and then cooled to −50° C. in order to precipitate the triethylamine hydrochloride. It is filtered and the filtrate is evaporated to dryness. The solid obtained is recrystallized from methanol. 4.1 g (0.0079 mole) of 1,3-bis[(5-p-chlorophenyl-2-oxo-piperidino)methyl]-2-thiourea are thus obtained. Yield: 68% of theory; M.P. 212°–213° C.

Analysis for C₂₅H₂₈Cl₂N₄O₂S: calculated: C 57.8%, H 5.4%, N 10.8%, Cl 13.7%, S 6.2%. found: C 57.8%, H 5.5%, N 10.7%, Cl 14.0%, S 6.0%.

The following compounds are prepared in the same manner:

(b) 1,3-bis[(2-oxo-pyrrolidino)methyl]-2-thiourea. (Compound No.25).

Yield: 68% of theory; M.P. 183°–184° C.

Analysis for $C_{11}H_{18}N_4O_2S$: calculated: C 48.9%, H 6.7%, N 20.8%, S 11.9%. found: C 48.8%, H 6.8%, N 20.8%, S 11.7%.

(c) 1,3-bis[(3-n-butyl-2-oxo-pyrrolidino)methyl]-2-thiourea. (Compound No.26).

Yield: 7% of theory; M.P. 119°-120° C.

I.R. spectrum (CHCl₃) in cm⁻¹: 2940, 2860, 1670, 1555, 1340, 1200, 1050.

NMR spectrum (CDCl₃+TMS):

| Chemical shift | Multiplicity | Integration | Attribution |
|---|---|---|---|
| 0.8-2.0 ppm | multiplet | 18H | (two butyl radicals) |
| 2.0-2.6 ppm | multiplet | 6H | (CH in the 3-position and CH₂ in the 4-position of the two pyrrolidino rings) |
| 3.58 ppm | multiplet | 4H | (CH₂ in the 5-position of the two pyrrolidino rings) |
| 5.12-5.25 ppm | multiplet | 4H | (CH₂ next to the two NH groups) |
| 8.76 ppm | broad | 2H | (two NH) |

(d) 1,3-bis[(3-n-butyl-2-oxo-pyrrolidino)methyl]-2-thiourea. (Compound No.27).

Yield: 1% of theory; M.P. 148°-149° C.

Compounds Nos.26 and 27 are two diastereoisomers separated by chromatography on silica.

I.R. spectrum (KBr) in cm⁻¹: 2940, 2860, 1670, 1555, 1340, 1215, 1040.

NMR spectrum (CDCl₃+TMS):

| Chemical shift | Multiplicity | Integration | Attribution |
|---|---|---|---|
| 0.7-1.8 ppm | multiplet | 18H | (two butyl radicals) |
| 1.8-2.5 ppm | multiplet | 6H | (CH in the 3-position and CH₂ in the 4-position of the two pyrrolidino rings) |
| 3.58 ppm | multiplet | 4H | (CH₂ in the 5-position of the two pyrrolidino rings) |
| 5.05 ppm | doublet | 4H | (CH₂ next to the two NH groups) |
| 8.08 ppm | broad multiplet | 2H | (two NH) |

(e) 1-[(hexahydro-2-oxo-1H-azepin-1-yl)methyl]-3-[(2-oxo-pyrrolidino)methyl]-2-thiourea. (Compound No.28).

A solution of 6.27 g (0.055 mole) of 1-aminomethyl-2-pyrrolidinone in 50 ml of methylene chloride is added slowly and with vigorous stirring to a solution of 3.8 ml (0.05 mole) of thiophosgene and 10.1 g (0.1 mole) of triethylamine in 50 ml of methylene chloride kept at −70° C. After the addition, the reaction mixture is allowed to return to ambient temperature and 7.8 g (0.005 mole) of 1-aminomethyl-hexahydro-2H-azepin-2-one are added slowly. Stirring is continued for 15 minutes and the reaction mixture is then cooled to −50° C. in order to precipitate the triethylamine hydrochloride. It is filtered and the filtrate is evaporated to dryness. The residue obtained is purified by chromatograhy on silica (eluent: chloroform). 5.9 g of 1-[(hexahydro-2-oxo-1H-azepin-1-yl)methyl]-3-[(2-oxo-pyrrolidino)methyl]-2-thiourea are obtained. Yield: 39% of theory; M.P. 147°-148° C.

Analysis for $C_{13}H_{22}N_4O_2S$: calculated: C 52.3%, H 7.4%, N 18.8%, S 10.7%. found: C 52.2%, H 7.4%, N 18.7%, S 10.1%.

II.2. Action of 1,1'-(thio)carbonyldiazoles on N-(aminoalkyl)lactams of formula (II)

II.2.1. Action of 1,1'-carbonyldiimidazole (a) 1-[(octahydro-2-oxo-1H-azonin-1-yl)methyl]-3-[(2-oxo-pyrrolidino)methyl]-urea. (Compound No. 29).

A solution of 8.1 g (0.05 mole) of 1,1'-carbonyldiimidazole in 20 ml of methylene chloride is added, with vigorous stirring, to a solution of 5.7 g (0.05 mole) of 1-aminomethyl-2-pyrrolidinone in 20 ml of methylene chloride cooled to −70° C., whereafter 8.5 g (0.05 mole) of 1-aminomethyloctahydro-2H-azonin-2-one in 20 ml of methylene chloride are also added. After the addition, the reaction mixture is heated under reflux for 2 hours. After evaporation of the solvent under reduced pressure, the residue obtained is purified by chromatography on silica (eluent: chloroform). 5.7 g (0.0184 mole) of 1-[(octahydro-2-oxo-1H-azonin-1-yl)methyl]-3-[(2-oxopyrrolidino)methyl]-urea are thus obtained.

Yield: 36.7% of theory; M.P. 149°-150° C.

Analysis for $C_{15}H_{26}N_4O_3$: calculated: C 58.0%, H 8.4%, N 18.1%. found: C 57.6%, H 8.1%, N 18.3%.

The following compounds are prepared in the same manner:

(b) Compound No.1 already mentioned. Yield: 47% of theory.

(c) Compound No.11 already mentioned. Yield: 14% of theory.

(d) 1,3-bis[(3-n-butyl-2-oxo-pyrrolidino)methyl]-urea. (Compound No.30).

Yield: 65% of theory; M.P. 186°-187° C.

Analysis for $C_{19}H_{34}N_4O_3$: calculated: C 62.3%, H 9.4%, N 15.3%. found: C 61.7%, H 9.2%, N 15.6%.

(e) 1-[(3-methyl-1-oxo-azaspiro[4.5]dec-2-yl)methyl]-3-[(2-oxo-pyrrolidino)-methyl]-urea. (Compound No.31). Yield: 18% of theory. I.R. spectrum (CHCl₃): 3380, 3000, 2970, 2930, 2860, 1670, 1555 cm⁻¹.

(f) 1-[(hexahydro-2-oxo-1H-azepin-1-yl)methyl]-3-[(2-oxo-pyrrolidino)methyl]-urea. (Compound No.32).

Yield: 34% of theory; M.P. 114°-115° C.

Analysis for $C_{13}H_{22}N_4O_3$: calculated: C 55.3%, H 7.9%, N 19.8%. found: C 55.3%, H 7.9%, N 19.5%.

(g) 1-[(hexahydro-2-oxo-1(2H)-azocinyl)methyl]-3-[(2-oxo-pyrrolidino)methyl]-urea. (Compound No.33).

Yield: 18% of theory; M.P. 118°-119° C.

Analysis for $C_{14}H_{24}N_4O_3$: calculated: C 56.7%, H 8.2%, N 18.9%. found: C 56.5%, H 8.1%, N 18.3%.

(h) Compound No.22 already mentioned; Yield: 75% of theory.

II.2.2. Action of 1,1'-thiocarbonyldiimidazole

A solution of 8.9 g (0.05 mole) of 1,1'-thiocarbonyldiimidazole in 60 ml of methylene chloride is added, with stirring, to a solution of 14.25 g (0.125 mole) of 1-aminomethyl-2-pyrrolidinone in 100 ml of anhydrous methylene chloride kept at a low temperature (−40° C.). After the addition, the reaction mixture is allowed to return to ambient temperature and the solvent is distilled under reduced pressure. The residue is recrystallized from methanol in the presence of activated carbon. 7.1 g (0.0263 mole) of 1,3-bis[(2-oxopyrrolidino)methyl]-2-thiourea, which is compound No.25 previously mentioned are thus obtained. Yield: 52.6% of theory.

II.3. Action of an alkyl haloformate

A solution of 1.63 g (0.015 mole) of ethyl chloroformate in 30 ml of anhydrous toluene is added slowly to a solution of 3.42 g (0.03 mole) of 1-aminomethyl-2-pyrrolidinone and 4.6 ml (0.032 mole) of triethylamine in 50 ml of anhydrous toluene, care being taken that the temperature does not exceed 10° C. After the addition, the reaction mixture is stirred for 2 hours at 50° C. in order to complete the reaction. It is then cooled to ambient temperature and the precipitate formed, which contains the desired product, is filtered off. This precipitate is suspended in methylene chloride and treated with gaseous ammonia. The ammonium chloride formed is filtered and the filtrate is evaporated to dryness under reduced pressure. The residue is recrystallized from isopropyl alcohol. 0.5 g (0.002 mole) of 1,3-bis[(2-oxopyrrolidino)methyl)]-urea, which is the previously mentioned compound No.1, are obtained. Yield: 13.3% of theory.

II.4. Action of an azide 14.3 g (0.124 mole) of trimethylsilyl azide (prepared by the method described by S. S. WASHBURNE et al., J. Organometall. Chem.33, (1971),153) are added with vigorous stirring and at ambient temperature to a solution of 16.15 g (0.1 mole) of 2-oxo-1-pyrrolidineacetyl chloride in 300 ml of benzene. The reaction mixture is then heated under reflux until no further nitrogen is liberated. The solution is evaporated to dryness and the (2-oxo-pyrrolidino)methyl isocyanate obtained is used as it is (the presence of an N=C=O group is verified by a band at 2260 cm$^{-1}$ in the infra-red spectrum). The isocyanate is dissolved in benzene to which a few ml of water are added. The mixture is stirred for 1 hour at ambient temperature. After evaporation under reduced pressure, the residue is recrystallized from isopropyl alcohol. 1.0 g (0.0039 mole) of 1,3-bis[(2-oxo-pyrrolidino)methyl]-urea, which is the previously mentioned compound No.1 is thus obtained. Yield: 8% of theory.

II.5. Action of 1,3-bis(hydroxyalkyl)-(2-thio)ureas

II.5.1. Use of 1,3-bis(hydroxymethyl)-urea 900 g (7.5 moles) of 1,3-bis(hydroxymethyl)-urea are added to a solution of 2550 g (30 moles) of 2-pyrrolidinone and 22.5 g (0.12 mole) of p-toluenesulfonic acid heated to 120° C. After dissolution, heating is continued for 5 minutes at 120° C. The reaction mixture is cooled to about 80° C. and poured while stirring into 5 liters of a 77.23 mixture of ethyl acetate and isopropyl alcohol.

The solid obtained is filtered, washed with 2 liters of the ethyl acetateisopropyl alcohol mixture and dried under reduced pressure. 763 g of the desired product are obtained, which are recrystallized from 3.5 liters of isopropyl alcohol to give 650 g (2.56 moles) of 1,3-bis[(2-oxo-pyrrolidino)methyl]-urea, which is the previously mentioned compound No1. Yield: 34% of theory.

The following compounds are prepared in the same manner:
Compound No.4 already mentioned. Yield: 16%
1,3-bis[(3-methyl-2-oxo-1-pyrrolidino)methyl]-urea (compound No.34). Yield: 49.6% of theory. M.P. 145°–146° C.

Analysis for $C_{13}H_{22}N_4O_3$ (M.W. 282): calculated: C 55.3%, H 7.8%, N 19.8%. found: C 55.2%, H 7.8%, N 19.8%.

1,3bis[(5,5-dimethyl-2-oxo-pyrrolidine)methyl]-urea (compound No.35).
Yield: 32.1% of theory. M.P. 180°–181° C.

Analysis for $C_{15}H_{26}N_4O_3$ (M.W. 310): calculated: C 58.1%, H 8.4%, N 18.0%. found: C 57.7%, H 8.2%, N 19.0%.

II.5.2. Use of 1,3-bis(1-hydroxyethyl)-urea 14.8 g (0.1 mole) of 1,3-bis(1-hydroxyethyl)-urea (prepared according to the method of E. NINAGAWA et al. Nippon Kagaku Zasshi, 87,(1966),1343; Chemical abstracts 67,(1967),43407) are added to a solution of 34 g (0.4 mole) of 2-pyrrolidinone and 0.3 g (0.0016 mole) of p-toluenesulfonic acid heated to 60° C. Heating is continued for 30 minutes. The obtained residue is recrystallized from an ethyl acetate-ethyl ether mixture to give 4 g (0.0142 mole) of 1,3-bis[1-(2-oxo-pyrrolidino)ethyl]-urea, which is compound No.11 previously mentioned. Yield: 14% of theory.

II.5.3. Use of 1,3-bis(hydroxymethyl)-2-thiourea 13.6 g (0.1 mole) of 1,3-bis(hydroxymethyl)-2-thiourea (prepared according to the method of Takeichi NISHIKAWA, J. Soc. Org. Synthetic Chem. (Japan), 11, (1953), 78; Chemical abstracts 47,(1953),7252) are added to a solution of 34 g (0.4 mole) of 2-pyrrolidinone and 0.3 g (0.0016 mole) of p-toluenesulfonic acid heated to 120° C. The mixture is heated for 1 hour at this temperature and then cooled to about 60° C. and poured into 80 ml of methanol. The obtained suspension is filtered while hot and 5.3 g (0.0196 mole) of 1,3-bis[(2-oxopyrrolidino)methyl]-2-thiourea, which is the compound No.25 previously mentioned, crystallize from this filtrate. Yield: 19.6% of theory.

The following compound is prepared in the same manner:
1,3-bis[(hexahydro-2-oxo-1H-azepin-1-yl)methyl]-2-thiourea (Compound No.36).
Yield: 18.5% of theory. M.P. 213°–214° C.

Analysis for $C_{15}H_{26}N_4O_2S$ (M.W. 326): calculated: C 55.2% H 8.0%, N 17.2% S 9.8%. found: C 55.5%, H 8.1%, N 17.1%, S 9.5%.

II.6. Action of formaldehyde and urea

A mixture of 17 g (0.2 mole) of 2-pyrrolidinone, 6 g (0.1 mole) of urea, 21 g (0.2 mole) of 35% formaldehyde and 0.5 g of p-toluenesulfonic acid in 120 ml of water is gradually heated to 70° C. The solution becomes turbid and gas evolves. The reaction mixture is then heated under reflux for 4 hours and then cooled and filtered. The filtrate is evaporated to dryness and purified by chromatograhy on silica using a mixture of chloroform and 5% methanol as the eluent. 3.4 g (0.0134 mole) of 1,3-bis[(2-oxo-pyrrolidino)methyl]-urea, which is the compound No.1 previously mentioned, are thus obtained. Yield: 13.4% of theory.

PHARMACOLOGICAL RESULTS

The compounds prepared above were tested pharmacologically, the results obtained are given below:

1. Action on mnemic processes (a) The action on mnemic processes is first shown by the ability of the compounds to improve a type of memory retention in rats. The principle of the active avoidance test developed in our laboratories and used for this purpose may be described as follows: the reaction of withdrawal of a rat's paw when subjected to an increasing and measured pressure is observed (see M. GREINDL and S. PREAT, Arch.Int.Pharmacodyn.Therap.223, (1976)(1), 168–171). The pressure at which the withdrawal reaction takes place is called the reaction threshold. This threshold is expressed by the figure read on a scale graduated in cm of the apparatus used (Analgesy-meter Ugo Basile, Milan) and thus corresponds to the minimum pressure which brings about withdrawal when applied to the animal's paw.

When tested 24 hours later, the control animals show no apparent retention of the previous test: avoidance takes place with a stimulation intensity comparable to that used the day before. Inversely, animals treated with a substance having a positive effect on mnemic processes (for example piracetam) show a significant degree of retention: the stimulus to which the rats react by a reflex of avoidance is statistically lower than that of the control animals.

A minimum of 20 rats is used per test (10 rats treated and 10 control rats) and the minimum dose lowering the stimulus below 11 graduations is defined as the active dose.

Subcutaneous administration of compounds of general formula (I) gave the results shown in the following Table I under these conditions. Examination of this Table shows that, in this test, all the tested products show a higher activity than piracetam, the action of which on the mnemic processes is well known.

TABLE

| Compound No. | Active dose mg/kg | Active dose mM/kg* |
|---|---|---|
| 1 | 0.0025 | $10^{-5}$ |
| 3 | 0.056 | $2 \cdot 10^{-4}$ |
| 4 | 0.0015 | $5 \cdot 10^{-6}$ |
| 5 | 0.338 | $10^{-3}$ |
| 6 | 1.83 | $5 \cdot 10^{-3}$ |
| 7 | 1.006 | $5 \cdot 10^{-3}$ |
| 8 | 1.41 | $5 \cdot 10^{-3}$ |
| 11 | 0.0014 | $5 \cdot 10^{-6}$ |
| 14 | 3.1 | $10^{-2}$ |
| 15 | 0.486 | $10^{-3}$ |
| 20 | 0.014 | $5 \cdot 10^{-5}$ |
| 21 | 0.0031 | $10^{-5}$ |
| 22 | 0.0067 | $2 \cdot 10^{-5}$ |
| 25 | 0.268 | $10^{-3}$ |
| 27 | 0.0038 | $10^{-5}$ |
| 33 | 1.48 | $5 \cdot 10^{-3}$ |
| 35 | 0.0062 | $2 \cdot 10^{-5}$ |
| 36 | 0.065 | $2 \cdot 10^{-4}$ |
| piracetam (reference compound) | 3.5 | $2.5 \cdot 10^{-3}$ |

*mM = millimole (b) The action on mnemic processes is also shown by the reduction of the spinal fixation time, a test which has been described in literature (T. J. CHAMBERLAIN et al., J.Neuro-Physiol.26, (1963,no. 4), 662–673; C. GIURGEA and F. MOURAVIEFF-LESUISSE, Arch.Int.Pharmacodyn.Therap.191, (1971,no. 2), 279) as an elementary memory model and which provides pharmacological reactivity in good correlation with clinical physiopathology. In the rat, after unilateral lesion of the cerebellum, there is a postural asymmetry of the hind paws. This asymmetry may persist, even after spinal section, if the animal has passed a sufficiently long time in this position.

This time, which is called the spinal fixation time, is 45 minutes under the experimental conditions applied here.

On the other hand, if the spinal section is performed before the expiry of this period of time, for example 35 minutes after the onset of the asymmetry, the latter disappears.

No animal treated with placebos retains asymmetry under these conditions.

Inversely, any product which allows the rats to retain the asymmetry (thus effecting spinal fixation) when the spinal section is performed after 35 minutes, is considered to be active.

Intraperitoneal administration of compounds of general formula (I) gave the results shown in the following Table II. The compounds were all tested at a dosage of 0.32 mM. The minimum active doses were not sought, except for compound No. 1 and for piracetam. For these two compounds, it is this minimum dose which is indicated in Table II. These results show, on the one hand, that compound No. 1 is more active than piracetam and, on the other hand, that, already at a dose of 0.32 mM/kg, the other compounds all have an activity of the same order of magnitude as piracetam, or even higher. By "number of animals" is to be understood the number of animals which responded positively to the test, in relation to the number of animals tested at the indicated dose:

TABLE II

| Compound No. | Active dose mg/kg | Active dose mM/kg | Number of animals |
|---|---|---|---|
| 1 | 25.0 | 0.1 | 7/11 |
| 4 | 99.0 | 0.32 | 4/6 |
| 7 | 160.9 | 0.32 | 4/6 |
| 8 | 90.4 | 0.32 | 4/7 |
| 20 | 90.2 | 0.32 | 3/7 |
| 22 | 108.2 | 0.32 | 5/7 |
| 23 | 99.2 | 0.32 | 3/6 |
| 24 | 166.2 | 0.32 | 3/7 |
| 34 | 90.2 | 0.32 | 3/6 |
| piracetam | 45.0 | 0.32 | 5/9 |

2. Protection against aggressions of the hypoxic type

Protection against aggressions of the hypoxic type was shown by a reduction of mortality induced by a curarizer, the action time of which is short, namely oxydipentonium chloride (Brevatonal). At the doses used, this curarizer brings about respiratory depression which, in turn, gives rise to a hypoxi-hypercapnic syndrome.

A compound capable of protecting the brain during this short period of hypoxia ensures survival. The compounds are administered to groups of 10 mice one hour before the injection of the curarizer. At the same time, a control group of 10 mice received physiological salt solution before the curarizer. This test has also been developed in our laboratories (see S. LEVIS et al., Arch.Int.Pharmacodyn.Therap.93, (1953,no. 1), 46–54).

Intraperitoneal administration of compounds of general formula (I) gave the results shown in the following Table III:

TABLE III

| Compound No. | Dose mg/kg (mM/kg) | Proportion of survivors Animals treated | Control animals |
|---|---|---|---|
| 1 | 2.5 (0.01) | 10/30 | 5/30 |

TABLE III-continued

| Compound No. | Dose mg/kg (mM/kg) | | Proportion of survivors | |
|---|---|---|---|---|
| | | | Animals treated | Control animals |
| | 8 | (0.032) | 14/20 | 3/20 |
| | 25 | (0.1) | 12/20 | 3/20 |
| 2 | 28 | (0.1) | 6/10 | 1/10 |
| 11 | 9 | (0.032) | 7/10 | 1/10 |
| 14 | 31 | (0.1) | 5/10 | 0/10 |
| 18 | 34 | (0.1) | 2/10 | 1/10 |
| | 107 | (0.32) | 6/10 | 1/10 |
| 26 | 38 | (0.1) | 7/10 | 1/10 |
| 28 | 30 | (0.1) | 2/10 | 2/10 |
| | 94 | (0.32) | 7/10 | 2/10 |
| 32 | 28 | (0.1) | 3/10 | 0/10 |
| | 89 | (0.32) | 6/10 | 0/10 |
| piracetam (reference) | 45 | (0.32) | 1/10 | 0/10 |
| | 142 | (1.0) | 4/10 | 2/10 |
| | 454 | (3.2) | 8/10 | 1/10 |

Therefore, the compounds tested exhibit a far higher activity than piracetam at the same or lower dose.

Toxicity

The compounds tested have a remarkably low toxicity. By way of example, the toxicity by intraperitoneal administration of compounds of the present invention is shown in the following Table IV:

TABLE IV

| Compound No. | Dose mM/kg - mouse* | mg/kg |
|---|---|---|
| 1 | >6 | >1530 |
| 2 | >3 | >846 |
| 4 | 3 | 930 |
| 5 | 3 | 1004 |
| 6 | >3 | 1099.5 |
| 7 | >3 | >1509 |
| 8 | >3 | >746 |
| 9 | 1 | 406 |
| 10 | >3 | >930 |
| 11 | >3 | >846 |
| 12 | >3 | 1215 |
| 13 | >3 | 1387.5 |
| 14 | >3 | 930 |
| 15 | >3 | 1459.5 |
| 16 | >3 | 1510.2 |
| 17 | 3 | 1255.8 |
| 18 | 2 | 676.8 |
| 19 | >3 | >1219 |
| 20 | >3 | >846 |
| 21 | >3 | >930 |
| 22 | >3 | >1014 |
| 23 | >3 | 931.2 |
| 24 | >3 | >1039 |
| 25 | >3 | >804 |
| 26 | >2 | >765.2 |
| 28 | 3 | 894 |
| 29 | 2 | 620 |
| 30 | >3 | >10009.5 |
| 31 | 2 | 672.8 |
| 32 | >3 | >846 |
| 33 | >3 | >888 |
| 34 | >6 | >1692 |
| 35 | >3 | >930 |

*Dose which brings about the death of one animal out of eight in Irwi. est (S. IRWIN, Gordon Research Conference on Medicinal Chemistry, Colt unior College, New London, 1959).

Furthermore, in the rat, the compounds tested also have a low toxicity when administered intravenously or orally, as shown by the results given in the following Table V:

TABLE V

| Compound No. | Method of administration | LD₅₀-mM/kg | LD₅₀ mg/kg (rat) |
|---|---|---|---|
| 1 | i.v.(*) | >22 | >5600 |
| | per os | >39 | >10000 |

TABLE V-continued

| Compound No. | Method of administration | LD$_{50}$-mM/kg | LD$_{50}$ mg/kg (rat) |
|---|---|---|---|
| piracetam | i.v. | >56 | >8000 |
| | per os | >70 | >10000 |

(*)Intravenously.

Therefore, the compounds of the present invention possess potentialities in the field of activity on the central nervous system, particularly in the neuropsychiatric sphere. They are also of interest as blood platelet antiaggregants.

The compounds of the present invention can be administered per os in the form of solid or liquid compositions for example, in the form of tablets, pills, sugar-coated pills, gelatine capsules, solutions, syrups and the like. Similarly, the compositions which can be administered parenterally are the pharmaceutical forms known for this purpose, for example, aqueous or oily solutions, suspensions or emulsions.

For rectal administration, the compositions are generally in the form of suppositories.

Pharmaceutical forms such as injectable solutions, injectable suspensions, tablets, drops and suppositories are prepared by conventional pharmaceutical methods. The compounds of the present invention are mixed with a pharmaceutically acceptable, non-toxic solid or liquid vehicle and optionally with a dispersing agent, a disintegrating agent, a lubricant, a stabilizing agent or the like. Preservatives, sweetening agents, coloring agents and the like may, if desired, be added.

Similarly, the solid or liquid pharmaceutical vehicles used in these compositions are well known. Solid pharmaceutical excipients for the preparation of tablets or capsules include, for example, starch, talc, calcium carbonate, lactose, sucrose, magnesium stearate and the like.

The percentage of active product in the pharmaceutical compositions may vary within very wide limits, depending upon the conditions of use and particularly upon the frequency of administration.

Human posology is of the order of 3×50 mg per day but may, if desired, vary from 10 mg to 4 g per day.

Example of a galenic composition

The following is an unlimiting example of a formulation for a tablet:
compound No. 1: 400 mg
starch: 61 mg
polyvinylpyrrolidone: 8 mg
talc: 26 mg
magnesium stearate: 5 mg

I claim:

1. A 1,3-disubstituted urea or 2-thiourea having the formula

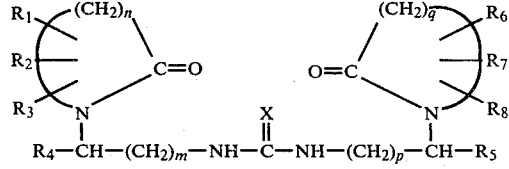

wherein
$R_1$, $R_2$, $R_3$, $R_6$, $R_7$ and $R_8$ represent independently hydrogen, alkyl having 1 to 4 carbon atoms, alkenyl having 2 to 4 carbon atoms, alkylene forming together with the carbon atom to which it is attached a cycloalkane ring having 5 or 6 carbon atoms, phenyl, naphthyl, halogen-substituted phenyl or halogen-substituted naphthyl, $R_4$ and $R_5$ represent independently hydrogen, alkyl having 1 or 2 carbon atoms or phenyl, n and q are independently 3, 4, 5, 6 or 7, m and p are independently 0, 1 or 2, and X is oxygen or sulfur.

2. A compound as claimed in claim 1, namely 1,3-bis[(2-oxo-pyrrolidino)-methyl]-urea.

3. A compound as claimed in claim 1, namely 1,3-bis[-(hexahydro-2-oxo-1H-azepin-1-yl)methyl]-urea.

4. A compound as claimed in claim 1, namely 1,3-bis[(4-p-chlorophenyl-3-methyl-2-oxo-pyrrolidino)methyl]-urea.

5. A compound as claimed in claim 1, namely 1,3-bis[(5-methyl-2-oxopyrrolidino)methyl]-urea.

6. A compound as claimed in claim 1, namely 1,3-bis[1-(2-oxo-pyrrolidino)-ethyl]-urea.

7. A compound as claimed in claim 1, namely 1,3-bis[2-(2-oxo-pyrrolidino)-ethyl]-urea.

8. A compound as claimed in claim 1, namely 1,3-bis[2-(2-oxo-pyrrolidino)-propyl]-urea.

9. A compound as claimed in claim 1, namely 1,3-bis[2-(2-oxo-pyrrolidino)-butyl]-urea.

10. A compound as claimed in claim 1, namely 1,3-bis[(3-n-butyl-2-oxopyrrolidino)methyl]-2-thiourea.

11. A compound as claimed in claim 1, namely 1-[(hexahydro-2-oxo-1H-azepin-1-yl)methyl]-3-[(2-oxopyrrolidino)methyl]-2-thiourea.

12. A compound according to claim 1, wherein each of n and q is 3.

13. A compound according to claim 1, wherein $R_1=R_6$, $R_2=R_7$, $R_3=R_8$, $R_4=R_5$, n=q and m=p.

14. A pharmaceutical composition having a beneficial activity on the mnemic processes and a protective activity against aggressions of the hypoxic type comprising a pharmaceutically effective amount of a 1,3-disubstituted urea or 2-thiourea having the formula

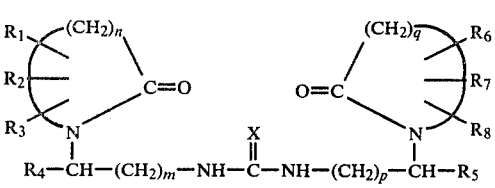

wherein $R_1$, $R_2$, $R_3$, $R_6$, $R_7$ and $R_8$ represent independently hydrogen, alkyl having 1 to 4 carbon atoms, alkenyl having 2 to 4 carbon atoms, alkylene forming together with the carbon atom to which it is attached a cycloalkane ring having 5 or 6 carbon atoms, phenyl, naphthyl, halogen-substituted phenyl or halogen-substituted naphthyl, $R_4$ and $R_5$ represent independently hydrogen, alkyl having 1 or 2 carbon atoms or phenyl, n and q are independently 3, 4, 5, 6 or 7, m and p are independently 0, 1 or 2 and X is oxygen or sulfur, and a pharmaceutically acceptable solid or liquid carrier.

15. A pharmaceutical composition according to claim 14, wherein $R_1=R_6$, $R_2=R_7$, $R_3=R_8$, $R_4=R_5$, n=q and m=p.

* * * * *